United States Patent [19]

Polony et al.

[11] 4,318,883

[45] Mar. 9, 1982

[54] PROCESS FOR COMBATING MICRO-ORGANISMS, AND NOVEL PHTHALOCYANINE COMPOUNDS

[75] Inventors: Rudolf Polony, Basel; Gerhard Reinert, Allschwil; Gerd Hölzle, Liestal; Andre Pugin, Riehen; Rodolphe Vonderwahl, Reinach, all of Switzerland

[73] Assignee: Ciba-Geigy Corporation, Ardsley, N.Y.

[21] Appl. No.: 121,955

[22] Filed: Feb. 15, 1980

Related U.S. Application Data

[63] Continuation of Ser. No. 888,589, Mar. 20, 1978, abandoned.

[30] Foreign Application Priority Data

Mar. 25, 1977 [CH] Switzerland .................... 3809/77

[51] Int. Cl.³ .......................... A61L 2/08; A61L 2/18
[52] U.S. Cl. ....................................... 422/22; 422/28; 422/37
[58] Field of Search ................. 422/22, 28, 32, 37; 8/1 XA

[56] References Cited

U.S. PATENT DOCUMENTS

| | | | |
|---|---|---|---|
| 1,476,233 | 12/1923 | Zell et al. ...................... | 424/257 X |
| 1,549,208 | 8/1925 | Mooser ......................... | 424/257 X |
| 1,614,201 | 1/1927 | Churchman .................... | 424/257 |
| 1,766,441 | 6/1930 | Lieske et al. .................. | 424/256 X |
| 2,051,057 | 8/1936 | Petti ............................. | 422/22 |
| 2,575,713 | 11/1951 | Johansson ..................... | 424/257 X |
| 3,305,559 | 2/1967 | Kuhne et al. .................. | 8/1 XA UX |
| 3,320,275 | 5/1967 | Dien et al. ..................... | 8/1 XA X |
| 3,622,263 | 11/1971 | Groll et al. .................... | 8/1 XA X |
| 3,674,783 | 7/1972 | Tobel ............................ | 8/1 XA X |
| 3,711,500 | 1/1973 | Groll ............................. | 8/1 XA X |
| 3,737,437 | 6/1973 | von Brachel et al. .......... | 8/1 XA X |
| 3,824,077 | 7/1974 | Razav ............................ | 8/1 XA X |
| 3,899,486 | 8/1975 | Horst ............................. | 8/1 XA X |
| 3,951,797 | 4/1976 | Seely ............................. | 210/63 R |
| 4,008,136 | 2/1977 | Williams ........................ | 210/63 R |
| 4,033,980 | 7/1977 | Meininger et al. ............. | 8/1 XA X |
| 4,081,239 | 3/1978 | Jefferies ........................ | 8/1 XA |

FOREIGN PATENT DOCUMENTS 908761 10/1962 United Kingdom ............... 424/246

OTHER PUBLICATIONS

Wallis et al. (I), "Photodynamic Inactivation of Enteroviruses", *J. of Bacteriology*; vol. 9, No. 1, 1/65, pp. 41-46.
Wallis et al. (II), "Irreversible Photosensitization of Viruses", *Virology*, 23, 1964, pp. 520-527.
*Chemical Engineering*, 9/1/75, p. 49.
*Chemie in Unserer Zeit*, No. 1, 1974, pp. 11-16.
Journal of Water Pollution Control Federation, Apr. 1977, pp. 575 & 583.
Venkataraman, "The Chemistry of Synthetic Dyes", vol. 4, 1971, pp. 502-505.
*Angewandte Chemie*, vol. 69, pp. 579-599.

*Primary Examiner*—Barry Richman
*Attorney, Agent, or Firm*—John P. Spitals

[57] ABSTRACT

A process for combating micro-organisms in or on organic or inorganic substrates and for protecting the said substrates against attack by micro-organisms, which comprises treating the substrates with a water-soluble phthalocyanine derivative, in the presence of oxygen and water and while irradiating with light in the infrared and/or visible range, antimicrobical agents containing water-soluble phthalocyanine compounds as well as new phthalocyanine compounds are described.

26 Claims, No Drawings

PROCESS FOR COMBATING MICRO-ORGANISMS, AND NOVEL PHTHALOCYANINE COMPOUNDS

This is a continuation of application Ser. No. 888,589 filed on Mar. 20, 1978, now abandoned.

The present invention relates to a process for combating micro-organisms, especially bacteria, in or on organic or inorganic substrates and for protecting the said substrates against attack by micro-organisms, and to agents for combating micro-organisms and also to novel phthalocyanine compounds.

It is known that certain dyes, for example eosin, Bengal Rose, methylene blue and others, have a so-called photodynamic action, i.e. on irradiation with light, they act as catalysts for the oxidation of various substrates with oxygen [see, for example, G. O. Schenck, Angew. Chem. 69, 579 (1957)]. Because of this property, the said dyes also have a certain antimicrobial action [see, for example, Venkataraman, The Chemistry of Synthetic Dyes, Volume 4 (1971) pages 502–505 and C. J. Wallis, J. L. Melnick, J. Bacteriol. 89, 41 (1965)].

It has now been found that a specific group of compounds, i.e. water-soluble phthalocyanine compounds, have, in the presence of oxygen and water and on irradiation with light, a particularly good action against micro-organisms, as a result of photodeactivation. Water-soluble phthalo-cyanine compounds, for example the copper, nickel and cobalt complexes of sulphonated phthalocyanine, but also metal-free sulphonated phthalocyanine, are well-known as dyes. Other phthalocyanine compounds preferably used in the process according to the invention are, however, novel.

The invention thus relates to a process for combating micro-organisms in or on organic or inorganic substrates and for protecting the said substrates against attack by micro-organisms and comprises treating the substrates with water-soluble phthalocyanine compounds, in the presence of oxygen and water and while irradiating with visible and/or infrared light.

The invention also relates to agents which are suitable for carrying out this process. The invention furthermore relates to novel phthalocyanine compounds and the use thereof as photodeactivators for micro-organisms.

The water-soluble phthalocyanine compounds required for carrying out the process according to the invention are preferably metal complexes but also phthalocyanines without a central atom.

If they are to have the necessary solubility in water, the phthalocyanine compounds mentioned must be substituted on the phenyl nuclei by one or more groups conferring solubility in water. These groups can be either acid or basic groups. Some examples of such groups are listed below, but this list in no way includes all the possible groups.

(a) Sulpho and carboxyl groups and their salts. There can be 1 to 4, and preferably 1.5 to 4, sulpho groups in the molecule. Salts are, in particular, alkali metal salts, ammonium salts or amine salts and in the case of the sulpho groups also salts with sulphonium and phosphonium bases. In addition, sulpho groups and carboxyl groups can also occur conjointly in one molecule.

(b) Groups of the formula

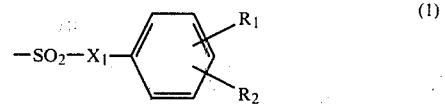

in which $X_1$ is oxygen or a —NH— or —N-alkyl radical and $R_1$ and $R_2$ independently of one another are hydrogen, a sulpho group and salts thereof, a carboxyl group and salts thereof or a hydroxyl group, at least one of the radicals $R_1$ and $R_2$ being a sulpho or carboxyl group or a salt thereof.

(c) Groups of the formula

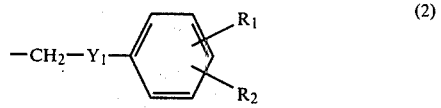

in which $Y_1$ is oxygen, sulphur or a —NH— or —N-alkyl radical and $R_1$ and $R_2$ are as defined under formula (1).

(d) Groups of the formula

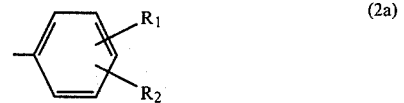

in which $R_1$ and $R_2$ are as defined under formula (1).

(e) Groups of the formulae $$-SO_2(CH_2)_n-SO_3M, \qquad (3)$$
$$-SO_2(CH_2)_n-OSO_3M \text{ and} \qquad (3a)$$
$$\begin{array}{c} R_7 \\ | \\ -SO_2N-(CH_2)_n-OSO_3M \end{array} \qquad (3b)$$

in which n is an integer from 2 to 12 and preferably the number 2, $R_7$ is a substituted or unsubstituted alkyl group having 1 to 6 carbon atoms, or hydrogen, and M is an alkali metal ion or ammonium ion.

(f) Groups of the formulae

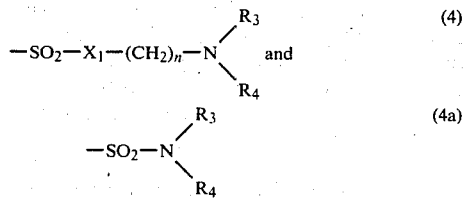

in which n is a number from 2 to 12, $X_1$ is oxygen or a —NH— or —N-alkyl group and $R_3$ and $R_4$ independently of one another are hydrogen, alkyl, hydroxyalkyl, cyanoalkyl, sulphoalkyl, carboxyalkyl or halogenoalkyl having 1 to 6 carbon atoms, unsubstituted phenyl or phenyl substituted by halogen, alkyl or alkoxy having 1 to 4 carbon atoms, sulpho or carboxyl, or $R_3$ and $R_4$ together with the nitrogen atom to which they are bonded form a saturated 5-membered or 6-membered heterocyclic ring, which additionally can also contain a nitrogen atom or oxygen atom as a ring member.

Amongst the 5-membered or 6-membered rings ($R_3+R_4$), the morpholine, piperidine, pyrazoline, piperazine and oxazolidine radical are preferred.

(g) Groups of the formulae

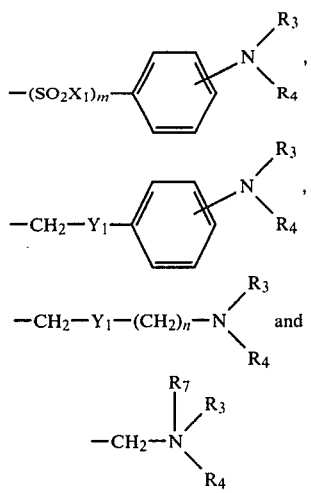

in which n, $R_3$, $R_4$ and $R_7$ are as defined above, m is 0 or 1, $X_1$ is oxygen or a —NH— or —N-alkyl group and $Y_1$ is oxygen, sulphur or a —NH— or —N-alkyl group.

(h) Groups of the formulae

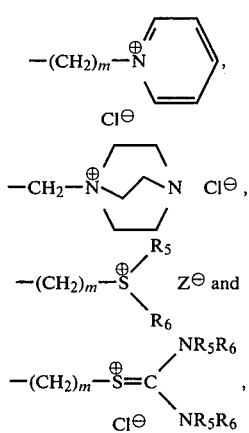

in which m is 0 or 1, Z is an anion, for example a chlorine, bromine, alkyl-sulphate or aralkyl-sulphate ion, and $R_5$ and $R_6$ independently of one another are a substituted or unsubstituted alkyl or aralkyl radical. The group of quaternary ammonium salts also includes those compounds which are obtained by quaternising groups listed under (f) and (g).

In the above formulae, $X_1$ and $Y_1$ are preferably —NH— or —N-alkyl. Halogen is preferably chlorine or bromine, especially chlorine.

The obtaining of an adequate solubility in water determines the number of substituents present in the molecule. If several groups conferring solubility in water are present in the molecule, these groups can be of the same type or different. As is customary in phthalocyanine chemistry, the degree of substitution does not necessarily have to be an integer, since products which are single compounds are not always formed from the method of preparation, for example sulphonation. In general, the total number of substituents per molecule is between 1 and 4.

The solubility in water of the particular phthalocyanine compound is adequate when the concentration of the compound in an aqueous solution is suitable for achieving a satisfactory microbicidal actions as subsequently set forth. A minimum solubility of 0.01 g/l can already be adequate but in general a minimum solubility of 0.1 to 20 g/l is advantageous. In addition to the groups conferring solubility which have been listed, all other groups which impart the required solubility in water to the phthalocyanines are also possible.

In addition to the groups conferring solubility in water, the phthalocyanines which can be used according to the invention can also contain yet further substituents, for example reactive radicals customary in dye chemistry, such as chloropyrazine, chloropyrimidine and, in particular, chlorotriazine radicals.

As already mentioned, either metal-free phthalocyanines or metal complexes thereof can be used in the process according to the invention. Metal complexes are those of all metals which form complexes with the phthalocyanine compounds. Preferred complexes, however, are those with aluminium, zinc, calcium, magnesium, iron-II, potassium and sodium, but especially aluminium, zinc, calcium and magnesium, in particular aluminium and zinc and very particularly aluminium.

The process according to the invention can be carried out particularly advantageously when the active compound employed is a water-soluble phthalocyanine of the formula $$(Me)_m(PC)(R)_v \qquad (10)$$

in which PC is the phthalocyanine ring system, v has any desired value between 1 and 4, Me is Zn, Fe(II), Ca, Mg, Na, K or AlX, in which X is an anion, especially a halide, sulphate, nitrate, acetate or hydroxyl ion, m is 0 or 1 and R is a group of the formula $$—SO_3Y, \qquad (11)$$

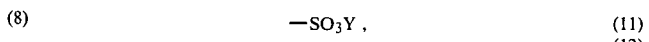

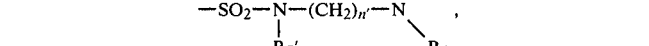

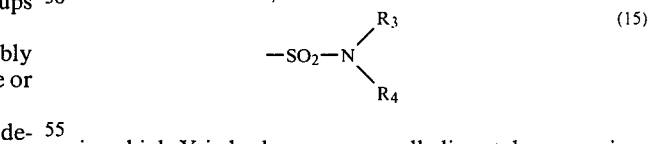

in which Y is hydrogen or an alkali metal, ammonium or amine ion, $R_7'$ is hydrogen or alkyl having 1 to 4 carbon atoms, n' is an integer from 2 to 6, $R_1$ and $R_2$ independently of one another are hydrogen, a sulpho group and salts thereof, a carboxyl group and salts thereof or a hydroxyl group and at least one of the radicals $R_1$ and $R_2$ is a sulpho or carboxyl group or a salt thereof, and $R_3$ and $R_4$ independently of one another are hydrogen, alkyl, hydroxyalkyl, cyanoalkyl, sulphoalkyl, carboxyalkyl or halogenoalkyl having, in each case, 1 to 6 carbon atoms, or phenyl, or $R_3$ and $R_4$ together with the nitrogen atom to which they are bonded are a saturated 5-membered or 6-membered heterocyclic ring, which additionally can also contain a nitrogen atom or oxygen atom as a ring member, and, when several radicals R are present in the molecule, these radicals can be identical or different, and all the radicals R are bonded to the phenyl nuclei of the phthalocyanine ring system.

Preferably, the process according to the invention is carried out with phthalocyanine derivatives containing acid substituents, and the metal complexes thereof, in particular with those which are substituted by sulpho and/or carboxyl groups, in particular with sulphonated phthalocyanines and metal complexes thereof, especially with those of the formula

(16)

in which PC is the phthalocyanine ring system, Y' is hydrogen or an alkali metal or ammonium ion, v is any desired number between 1 and 4 (the degree of sulphonation), m is 0 or 1 and Me is Zn, Fe(II), Ca, Mg, Na, K or AlX, in which X is an anion, especially a halide, sulphate, hydroxyl or acetate ion.

In the case of aluminium complexes, the molecule also contains an anion X in order to saturate the third valency of the aluminium ion; this anion is of no significance for the microbicidal action and is usually identical to the anion of the aluminium compound which has been used to prepare the complex.

Particularly preferred compounds are the phthalocyaninesulphonic acids and their derivatives (for example alkali metal salts, ammonium salts or amine salts) and their Zn, Al, Ca and Mg complexes, especially the Zn complexes but in particular the Al complexes. The number of sulpho groups present in the phthalocyanine molecule can be between 1 and 4 and especially between 1.3 and 4. As a rule, mixtures are obtained from the sulphonation of phthalocyanines (see Preparation), so that the number of sulpho groups is an average value and does not have to be an integer (degree of sulphonation). A degree of sulphonation of about 2 is particularly advantageous for the process according to the invention. Phthalocyanines which are preferably to be employed are, therefore, for example:

(17)

and

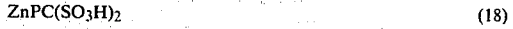

(18)

(PC=phthalocyanine) and their salts.

The phthalocyanines which contain basic substituents and are substituted by groups of the formula (4) or (4a) mentioned initially under (f) also have a very good action. The total molecule advantageously contains 1 to 4, and preferably 2 to 4, of these groups. Preferred groups are those in which n is 2 to 6 and R₃ and R₄ are hydrogen or lower alkyl (1 to 4 carbon atoms), or together are a piperidine or morpholine ring. These phthalocyanines containing basic substituents can be metal-free or can contain, as central atoms, the same metals as the phthalocyaninesulphonic acids described above. In this case also the zinc complexes, but especially the aluminium complexes, are preferred.

Phthalocyanines of this type which can be employed in the process according to the invention are, for example, of the formula

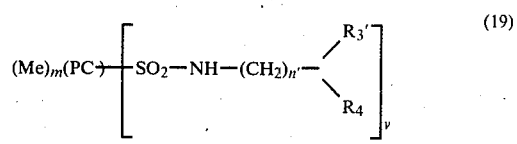

(19)

in which PC, Me and m are as defined in formula (10), n' is an integer between 2 and 6, R₃' and R₄' independently of one another are hydrogen, phenyl, sulphophenyl, carboxyphenyl or alkyl, hydroxyalkyl, cyanoalkyl, sulphoalkyl, carboxyalkyl or halogenoalkyl having, in each case, 1 to 6 carbon atoms, or together with the nitrogen atom are the morpholine ring, and v is a number between 1 and 4, and, if v>1, the radicals

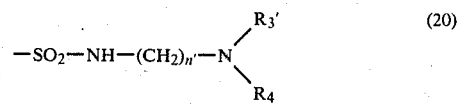

(20)

present in the molecule can be identical or different.

Further phthalocyanines which are very suitable for use in the process according to the invention are of the formula

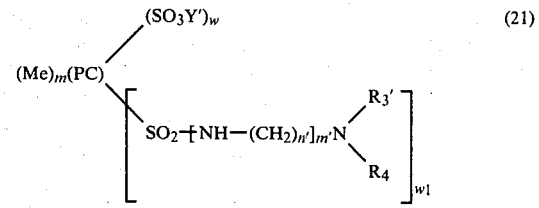

(21)

in which PC, Me and m are as defined in formula (10), Y' is hydrogen or an alkali metal or ammonium ion, n' is an integer between 2 and 6, R₃' and R₄' independently of one another are hydrogen, phenyl, sulphophenyl, carboxyphenyl or alkyl, hydroxyalkyl, cyanoalkyl, sulphoalkyl, carboxyalkyl or halogenoalkyl having, in each case, 1 to 6 carbon atoms, or together with the nitrogen atom are the morpholine ring, m' is 0 or 1 and w and w₁ independently of one another are any desired number between 0.5 and 3, and w+w₁ is at least 1, but at most 4.

Like the sulphonated phthalocyanines, the phthalocyanine compounds of the formulae (19) and (21) can be metal-free; however, the metal complexes, especially those with Ca, Mg, Zn and Al, in particular those with Zn and especially with Al, are preferred.

The phthalocyanine compounds which can be employed in the process according to the invention require the presence of oxygen and water and also irradiation by visible and/or infrared light in order to develop their antimicrobial activity. The process is therefore generally carried out in aqueous solutions or on damp substrates and atmospheric oxygen serves as the source of oxygen. In the presence of reducing agents or so-called quenchers, the active substances loose their action.

Illumination can be by an artificial light source which supplies light in the infrared and/or visible range, or alternatively by sunlight. A good effect is achieved, for example, by light in the range between about 600 and 2,500 nm. Thus, for example, irradiation can be by means of a commercially available filament lamp or by means of an infrared lamp with a λ$_{max}$ at about 1,200 to 1,600 nm. The intensity of illumination can vary between wide limits. It depends on the concentration of the active substance and on the nature of the substrate and on the substances additionally present which have an influence on the luminous efficiency. As a further parameter, the exposure time can be varied, i.e. for the same effect, a longer exposure is required at a lower light intensity than at a higher intensity. In general, depending on the field of application, exposure times of a few minutes up to several hours are possible.

If the process is carried out in an aqueous bath (for example disinfecting of textiles), either the irradiation with light can be carried out direct in the treatment bath, by means of an artificial light source located within or outside the said bath, or the substrates, in the damp state, can subsequently either also be illuminated by an artificial light source or exposed to sunlight.

Good antimicrobial effects can already be achieved with lower concentrations of active substance, for example with 0.01 ppm. A concentration of between 0.05 and 100, and preferably 0.01 and 50, ppm is preferred, depending on the field of application and depending on the phthalocyanine derivative employed. Since the active substances are dyes, the upper concentration limit is given by the value above which, on the one hand, an undesired staining of the substrates and, on the other hand, a decrease in the action, would be observed. The poorer action results from the increasing absorption of light in the coloured application solutions and the fact that the light intensity resulting therefrom is too low for the photodynamic oxidation. The upper concentration limit is thus restricted by the strength of the inherent colour of the agents employed, but can be 1,000 ppm and above.

The phthalocyanine compounds employed in the process according to the invention have an exceptionally broad spectrum of activity against micro-organisms. Thus, it is possible by means of the process according to the invention to combat, in particular, Gram-positive and Gram-negative bacteria and to protect diverse substrates against attack by these bacteria. However, an action against fungi, viruses and algae can also be observed.

In the process according to the invention it is possible additionally to add substances which increase the action, inter alia electrolytes, for example inorganic salts, say sodium chloride, potassium chloride, sodium sulphate, potassium sulphate, sodium acetate, ammonium acetate, alkali metal phosphates and alkali metal tripolyphosphates, especially sodium chloride. These salts can be added to the agents according to the invention or can be added direct during the application process, so that they are present in the application solution in a concentration of preferably 0.1 to 10%.

Because of the broad spectrum of action against microorganisms, which has been mentioned, the process according to the invention and the agents according to the invention can be employed in a number of fields of application, examples of which are given below.

An important application is the disinfecting of textiles of synthetic or natural origin. Thus, goods for washing, in domestic use or in industry, can be disinfected with the aid of the process according to the invention. For this purpose, the goods for washing can be treated with aqueous solutions of water-soluble phthalocyanine derivatives whilst irradiating with light, in the abovementioned manner. The treatment liquor can advantageously contain the phthalocyanine dye in a concentration of 0.1 to 50 mg/l. Disinfecting can advantageously also be carried out together with the washing process. For this purpose, the goods to be washed are treated with a wash liquor which contains conventional detergent substances, one or more water-soluble phthalocyanine derivatives and, if desired, inorganic salts and/or further substances having an antimicrobial action. The washing process can be carried out manually, for example in a tub, or in a washing machine. The necessary irradiation can take place during the washing process, by means of suitable light sources, or the damp washed goods can also subsequently, for example during drying, either be irradiated by means of a suitable artificial light source or simply exposed to sunlight.

The antimicrobial active compounds can be added to the disinfecting or washing liquor direct. However, they can also be incorporated into soaps or washing powders, which contain known mixtures of detergent substances, for example soap in the form of chips and powder, synthetic substances, soluble salts of sulphonic acid half-esters of higher fatty alcohols, arylsulphonic acids which are substituted by higher alkyl and/or polysubstituted by alkyl, sulphocarboxylic acid esters of medium to higher alcohols, fatty acid acylaminoalkyl- or acylaminoaryl-glycerolsulphonates, phosphoric acid esters of fatty alcohols and the like, builders, for example alkali metal polyphosphates and polymetaphosphates, alkali metal pyrophosphates and alkali metal salts of carboxymethylcellulose, and other soil redeposition inhibitors, and also alkali metal silicates, nitrilotriacetic acid, ethylenediaminetetraacetic acid, foam stabilisers, such as alkanolamides of higher fatty acids, and also, if desired, antistatic agents, superfatting skin protection agents, such as lanolin, enzymes, perfumes and dyes, fluorescent brighteners and further inorganic salts and/or further antimicrobial active compounds.

Care must be taken that the wash liquors or washing agents do not contain any reducing agents since otherwise the oxygen necessary for the antimicrobial activity of the phthalocyanines is not available.

The process according to the invention can also be used to provide textiles with an antimicrobial finish, since the phthalocyanine derivatives absorb well onto the fibres and thus ensure a long-lasting effect.

A further field of application of the process according to the invention and of the agents according to the invention is the disinfecting of hospital laundry and medical commodities and equipment and also of floors, walls and furnishings in hospitals. The disinfecting of hospital laundry can be carried out in the manner described above for general goods for washing. The other articles and also floors and wall surfaces can be treated with aqueous solutions which contain water-soluble phthalocyanine compounds and, during the treatment or subsequently, irradiated with suitable light sources. The disinfecting solutions can additionally also contain detergent substances, other compounds having an antimicrobial action and/or inorganic salts.

Examples of further fields of application for the process according to the invention are:

Disinfecting of swimming pools. The requisite exposure to light can be effected by means of installed lamps or simply by sunlight. Because of the low toxicity of the phthalocyanines and because of the small amounts which are necessary for effective disinfecting of the water and to free the pool from algae (for example 0.1 to 1 ppm), the phthalocyanines according to the invention are outstandingly suitable for this application.

Disinfecting of effluents from sewage treatment plants.

The abovementioned application possibilities are merely listed as examples for the very broad applicability of the process according to the invention.

The present invention also relates to agents, for combating micro-organisms, which contain the water-soluble phthalocyanine active compounds which can be employed according to the invention. Such agents can be solid or liquid and in addition to the active compound can also contain other ingredients, for example water, salts and also conventional formulating additives. Washing agents according to the invention contain, in addition to the active compound, conventional detergent substances and washing agent additives, such as those listed above by way of example. The washing agents advantageously contain the active compound in an amount of 0.0005 to 1.25 percent by weight, based on the total agent.

Some of the water-soluble phthalocyanine active compounds described above are novel. The present invention therefore also relates to the novel phthalocyanine compounds of the formula $$Me'(PC)(R')_v \quad (22)$$

in which PC is the phthalocyanine ring system, v has any desired value between 1 and 4, Me' is Na, K, Mg or AlX, in which X is an anion, and R' is a group of the formula

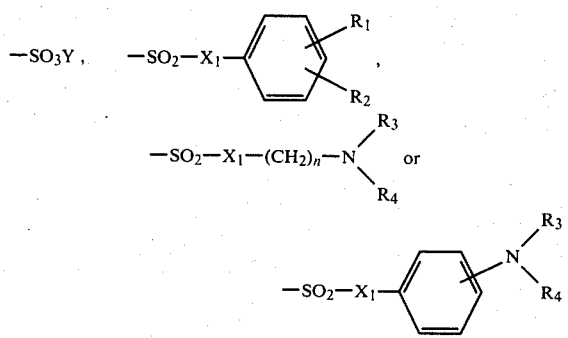

in which Y is hydrogen or an alkali metal, ammonium or amine ion, $X_1$ is oxygen or a NH group, n is a number from 1 to 12, $R_1$ and $R_2$ independently of one another are hydrogen, a sulpho group and salts thereof, a carboxyl group and salts thereof or a hydroxyl group and at least one of the radicals $R_1$ and $R_2$ is a sulpho or carboxyl group or a salt thereof, and $R_3$ and $R_4$ independently of one another are hydrogen, alkyl, hydroxyalkyl, cyanoalkyl or halogenoalkyl, having 1 to 6 carbon atoms, or $R_3$ and $R_4$ together with the nitrogen atom to which they are bonded are a saturated 5-membered or 6-membered heterocyclic ring which additionally can also contain a nitrogen atom or oxygen atom as a ring member, and all the radicals R are bonded to the phenyl nuclei of the phthalocyanine ring system, and the use thereof as photodeactivators for micro-organisms and to processes for the preparation of these compounds.

Further compounds which are novel and a subject of the invention are those of the formula $$Me'(PC)(R)_v \quad (23)$$

in which PC is the phthalocyanine ring system, v has any desired value between 1 and 4, Me' is Na, K, Ca, Mg or AlX, in which X is an anion, preferably a halide, sulphate, nitrate, acetate or hydroxyl ion, and R is a group of the formula

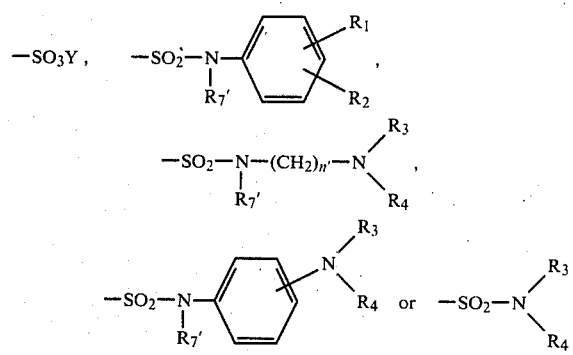

in which Y is hydrogen or an alkali metal, ammonium or amine ion, $R_7'$ is hydrogen or alkyl having 1 to 4 carbon atoms, n' is an integer from 2 to 6, $R_1$ and $R_2$ independently of one another are hydrogen, a sulpho group and salts thereof, a carboxyl group and salts thereof or a hydroxyl group and at least one of the radicals $R_1$ and $R_2$ is a sulpho or carboxyl group or a salt thereof, and $R_3$ and $R_4$ independently of one another are hydrogen, alkyl, hydroxyalkyl, cyanoalkyl, sulphoalkyl, carboxyalkyl or halogenoalkyl, having, in each case, 1 to 6 carbon atoms, or phenyl, or $R_3$ and $R_4$ together with the nitrogen atom to which they are bonded are a saturated 5-membered or 6-membered heterocyclic ring which additionally can also contain a nitrogen atom or oxygen atom as a ring member, and the radicals R are bonded to the phenyl nuclei of the phthalocyanine ring system and can be identical or different, when $v > 1$.

Preferred compounds within the range of the compounds of the formula (23) are those of the formula

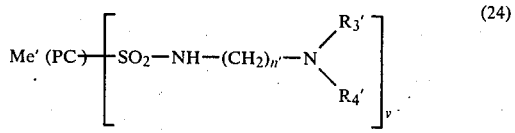

in which PC, Me', n' and v are as defined in formula (23) and $R_3'$ and $R_4'$ independently of one another are hydrogen, phenyl, sulphophenyl, carboxyphenyl or alkyl, hydroxyalkyl, cyanoalkyl, sulphoalkyl, carboxyalkyl or halogenoalkyl having, in each case, 1 to 6 carbon atoms, or together with the nitrogen atom are the morpholine ring.

Preferred compounds are those of the formula $$Me'(PC)(SO_3Y)_{v'} \quad (25)$$

in which Me', PC and Y are as defined above and v' has any desired value between 1 and 4, especially between 1.5 and 4.

Compounds of particular interest are those of the formula $$Al\ X'(PC)(SO_3Y)_{v'} \quad (26)$$

in which PC, Y and v' are as defined in formula (25) and X' is an anion from the group comprising $OH^-$, $SO_4^{2-}$, $Cl^-$, $Br^-$ and $CH_3COO^-$.

In this formula X' is preferably $Cl^-$, Y is hydrogen, sodium or potassium and v' is any desired number between 1 and 4.

The phthalocyanine compounds described above can also be prepared according to processes which are known per se.

In order to introduce substituents conferring solubility in water, the unsubstituted phthalocyanine or metal complexes thereof can be used as the starting material. Sulphonation (for example with 26% strength oleum) results in the corresponding sulphonic acids, products of different degrees of sulphonation being formed depending on the sulphonation time and temperature. Sulphonation of the unsubstituted phthalocyanine, for example at 45° to 60° C., gives the disulphonic acid. The conversion of the products into salts can be effected in a known manner.

Reaction of unsubstituted metal-free or metallised phthalocyanines with chlorosulphonic acid gives the corresponding sulphochloride compounds. Reaction of the resulting sulphochloride-phthalocyanines with correspondingly substituted aliphatic or aromatic amines or alcohols or phenols gives the phthalocyanines which are substituted by sulphonamide groups or, respectively, sulphonic acid ester groups of the formulae (1), (4), (3b) or (5, m=1). Saponification of the sulphochloride compounds results in the corresponding sulphonic acids.

Carboxyl groups can be introduced into the unsubstituted phthalocyanines by reaction with phosgene and aluminium chloride and hydrolysis of the acid chloride formed or by reaction with trichloroacetic acid. The acid chlorides can also be converted in a known manner into other water-soluble carboxylic acid derivatives. Products with mixed substituents (sulpho groups and carboxyl groups) can be obtained by a suitable combination of the processes described. Phthalocyanines substituted by carboxyl groups can also be prepared by synthesis from trimellitic acid.

Phthalocyanines which are substituted by groups of the formulae (2), (6) or (6a) can be obtained by chloromethylation of unsubstituted metal-free or metallised phthalocyanines, for example by reaction with paraformaldehyde or bis-chloromethyl ether and anhydrous aluminium chloride in the presence of triethylamine, and subsequent reaction of the chloromethyl compounds with correspondingly substituted anilines, phenols or thiophenols or amines, alcohols or mercaptans. The reaction of the chloromethyl intermediates mentioned with pyridine, 1,4-diazabicyclo-[2.2.2]-octane or with unsubstituted or correspondingly substituted tetraalkylthioureas gives phthalocyanines which are substituted by groups of the formulae (7, m=1), (7a) or (9, m=1) respectively. The chloromethyl compounds mentioned can also be reacted with substituted or unsubstituted alkyl sulphides to give the corresponding alkylthiomethyl compounds and the latter can be reacted with strong alkylating agents to give phthalocyanines which contain ternary groups of the formula (8, m=1).

Phthalocyanines which contain groups of the formulae (7, 8 or 9, m=0) can be prepared from the corresponding chlorine-substituted phthalocyanines, which are obtainable by direct chlorination of the unsubstituted phthalocyanines, by the processes described for the reaction of the chloromethyl compounds.

Phthalocyanines which are substituted by groups, conferring solubility in water, of the formulae (2a) or (5, m=0) can also be obtained, for example, when the correspondingly substituted phthalic anhydride or phthalodinitrile is used as the starting material and this is reacted in a known manner to give the phthalocyanine ring system. When substituted phthalodinitrile is used, this, if desired together with a metal salt, is cyclised in the melt or in solution or suspension to give the phthalocyanine ring system. When the corresponding phthalic anhydride is used, urea and, if appropriate, a catalyst, for example boric acid or ammonium molybdate, are additionally added before the reaction. Other substituted phthalocyanines, for example including the sulphonated phthalocyanines, can also be obtained in this way.

Some metal complexes of substituted phthalocyanines can not be prepared simply by substitution (as described above) of the unsubstituted complexes or by ring synthesis. In this case, the correspondingly substituted metal-free compounds can first be prepared and these can then be reacted with a metal salt or metal alcoholate in a solvent. Solvents which can be used are, for example, mixtures of water and organic solvents, especially including tertiary amines or also anhydrous solvents, for example pyridine or chlorobenzenes. This mode of preparation is chosen, in particular, for complexes which can be hydrolysed relatively easily, for example those of the alkali metals and alkaline earth metals.

Metal complexes can, of course, also be converted into other metal complexes; these can likewise be hydrolysed to metal-free phthalocyanine compounds with the aid of acids.

In the examples which follow, which illustrate the preparation of the water-soluble phthalocyanine compounds which can be employed according to the invention, and also the process according to the invention itself, all percentages are by weight unless otherwise stated. The abbreviation PC represents unsubstituted phthalocyanine in all examples.

EXAMPLE 1

0.67 g of metal-free phthalocyaninedisulphonic acid is dissolved in 100 ml of a mixture of pyridine/water (1:1) and 0.27 g of aluminium chloride is added. The solution is refluxed for 2 hours and evaporated in a rotary evaporator. The residue is taken up in 75 ml of water and the solution is neutralised with 1 N ammonia and evaporated again, whereupon the aluminium complex of phthalocyaninedisulphonic acid remains.

EXAMPLE 1a 2.66 g of aluminium chloride are added to a solution of 6.76 g of phthalocyaninedisulphonic acid, with an absorption maximum of 612 nm in a buffer solution of pH 7 (0.01 mol/l of sodium hydrogen phosphate/0.007 mol/l of potassium dihydrogen phosphate), in 500 ml of a 1:1 pyridine/water mixture. The solution is refluxed for 2 hours and then evaporated in a rotary evaporator. The residue is taken up in 75 ml of water and the solution is neutralised with ammonia. The aluminium complex of disulphonated phthalocyanine with an absorption maximum of 675 nm (buffer solution of pH 7) is obtained.

EXAMPLE 2

The following metal complexes of phthalocyaninedisulphonic acid (S=a sulphonic acid group): $ZnPCS_4$, $ZnPCS_2$, $MgPCS_2$, $MgPCS_{3-4}$, $FePCS_2$, $FePCS_{3-4}$, $CuPCS_2$, $NiPCS_2$, $MnPCS_2$, $CaPCS_2$, $CaPCS_{3-4}$, $CrClPCS_2$, $CdPCS_2$, $SnPCS_2$, $BaPCS_2$, $Bi(NO_3)PCS_2$, the sodium complex of phthalocyaninedisulphonic acid and the potassium complex of phthalocyaninedisulphonic acid, are obtained by the process described in Example 1 by reacting the free phthalocyaninesulphonic acids with the equivalent amount of $Zn(CH_3COO)_2$, $MgCl_2$, $FeSO_4$, $CuSO_4$, $NiCl_2$, $Mn(CH_3COO)_2$, $CaCl_2$, $CrCl_3$, $CdCl_2$, $SnCl_2$, $BaCl_2$, $Bi(NO_3)_3$, $NaOCH_3$ and $KOCH_3$ respectively.

EXAMPLE 2a

The procedure indicated in Example 1a is repeated, but salts of Mg, Ca or Fe(II) are used, affording the corresponding phthalocyanines listed in Table 1 below.

TABLE 1

| Metal salt | Phthalocyanine derivative | λ max in H$_2$O, pH 9 (nm) |
|---|---|---|
| MgCl$_2$ | Mg (PC)(SO$_3$H)$_2$ | 669 |
| CaCl$_2$ | Ca (PC)(SO$_3$H)$_2$ | 653 |
| FeSO$_4$ | Fe (PC)(SO$_3$H)$_2$ | 662 |

EXAMPLE 3

(a) 52.5 g of phthalic anhydride, 64 g of urea, 1 g of ammonium molybdate and 27 g of sodium m-xylenesulphonate are stirred in 175 g of trichlorobenzene and the resulting mixture is mixed with a suspension of 15 g of anhydrous aluminium chloride in 25 g of trichlorobenzene. After stirring for 6 hours at 200° to 205° C., 27 g of urea and 50 g of trichlorobenzene are added and the mixture is stirred for a further 5 hours at 200° to 205° C. The suspension is filtered cold and the residue is washed with chlorobenzene and methanol and then purified by boiling thoroughly in dilute hydrochloric acid and in dilute sodium hydroxide solution and finally in dilute hydrochloric acid again. After drying, 34 g of an aluminium complex of phthalocyanine are obtained and according to analysis this has the formula $$C_{32}H_{16}N_8AlCl.2H_2O$$

(b) 20 g of this aluminium complex of phthalocyanine are stirred in 220 ml of 30% strength oleum for 8 hours at 73 to 75° C. and, after cooling to room temperature, the resulting solution is poured onto ice and 10% strength sodium chloride solution, the suspension is filtered and the residue is washed with 10% strength sodium chloride solution and then with 1 N hydrochloric acid and dried in vacuo at 90° C. Yield: 22 g. The product has the formula $$AlCl(PC)(SO_3H)_2 \quad (301)$$

λmax = 671 nm (in H$_2$O, pH 9).

Any other desired aluminium salt can also be employed in step (a) in place of aluminium chloride. Depending on the nature of the anion, aluminium complexes of phthalocyanine derivatives in which the third valency of the aluminium is saturated by any other desired anion (for example sulphate, acetate, hydroxyl and the like) instead of by chlorine are obtained in this way, in this example and in the examples which follow.

EXAMPLE 4

(a) 20 g of the aluminium complex of phthalocyanine prepared according to Example 3(a) are introduced at 20° to 25° C. into 140 ml of chlorosulphonic acid and the mixture is stirred for 30 minutes. The temperature is then raised to 135° to 140° C. in the course of 2 hours. After stirring for 4 hours, the reaction mixture is cooled to room temperature and poured onto ice. The suspension is filtered and the material on the filter is washed acid-free with ice-water.

(b) The moist suction filter cake is stirred in 500 ml of ice-water, 3.2 g of ethanolamine are added and the pH of the mixture is kept at 8 to 9 by adding 10% strength sodium hydroxide solution, with stirring. After stirring for 2 hours at 0° to 25° C., the temperature is raised to 60° to 70° C. and this temperature is maintained for 5 hours. All of the product is precipitated by adding sodium chloride and is filtered off and dried in vacuo at 70° to 80° C. The compound thus obtained has the formula

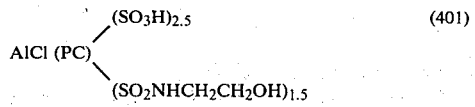
(401)

λmax = 677.5 nm (in H$_2$O, pH 7).

If the aluminium complex of the phthalocyanine-tetrasulphochloride obtained according to Example 4(a) is reacted in an analogous manner with other amines, the compounds of the general formula

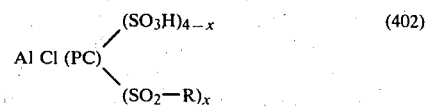
(402)

listed in Table 2 which follows are obtained.

TABLE 2

| Formula No. | R | x | Amine used |
|---|---|---|---|
| 403 | —NH$_2$ | 1 | NH$_2$OH |
| 404 | —NHCH$_3$ | 1 | H$_2$NCH$_3$ |
| 405 | —N(CH$_2$CH$_2$OH)$_2$ | 1,5 | HN(CH$_2$CH$_2$OH)$_2$ |
| 406 | —NHCH$_2$CH$_2$N(CH$_3$)$_2$ | 3 | H$_2$NCH$_2$CH$_2$N(CH$_3$)$_2$ |
| 407 | —NHCH$_2$CH$_2$CH$_2$N(CH$_3$)$_2$ | 4 | H$_2$NCH$_2$CH$_2$CH$_2$N(CH$_3$)$_2$ |
| 408 | —N(CH$_3$)CH$_2$CH$_2$SO$_3$H | 2 | HN(CH$_3$)CH$_2$CH$_2$SO$_3$H |
| 409 | —NHCH$_2$CH$_2$OSO$_3$H | 2 | H$_2$NCH$_2$CH$_2$OSO$_3$H |
| 410 | —NH(CH$_2$)$_6$COOH | 1 | H$_2$N(CH$_2$)$_6$COOH |
| 411 | —N(CH$_3$)—C$_6$H$_5$ | 1 | HN(CH$_3$)—C$_6$H$_5$ |

TABLE 2-continued

| Formula No. | R | x | Amine used |
|---|---|---|---|
| 412 | —NH—⌬—COOH | 1,5 | H₂N—⌬—COOH |
| 413 | —NH—⌬(SO₃H) | 1 | H₂N—⌬(SO₃H) |
| 414 | —NH—⌬—NH—[triazine-Cl]—NH—⌬—SO₃H | 1 | H₂N—⌬—NH—[triazine-Cl]—NH—⌬—SO₃H |
| 415 | —NHCH₂CH₂NH—[triazine-Cl]—NH—⌬(SO₃H)(SO₃H) | 2 | H₂NCH₂CH₂NH—[triazine-Cl]—NH—⌬(SO₃H)(SO₃H) |
| 416 | —N(morpholine) | 1 | HN(morpholine) |

EXAMPLE 5

20 g of the aluminium complex of the phthalocyanine-tetrasulphochloride prepared according to Example 4(a) are introduced into 500 ml of water and hydrolysed by adding sodium hydroxide solution, at 60° to 70° C., and the reaction mixture is then evaporated to dryness. This gives 25 g of the aluminium complex of phthalocyanine-tetrasulphonic acid (Na salt) of the formula $$\text{Al Cl (PC)}\text{—}(SO_3Na)_4 \qquad (501)$$

$\lambda max = 672.75$ nm (in $H_2O$, pH 9).

The same compound is also obtainable by sulphonation of the aluminium complex of the unsubstituted phthalocyanine (obtainable according to Example 3(a) with 60% strength oleum at 70° to 75° C.

EXAMPLE 6

(a) 20 g of the aluminium complex of phthalocyanine prepared according to Example 3(a) are introduced at 25° C. into 150 ml of chlorosulphonic acid and the mixture is stirred for 30 minutes. The reaction mixture is then warmed to 65° to 70° C. and 32 ml of thionyl chloride are added dropwise in the course of 20 minutes. The temperature is then raised to 110° to 115° C. in the course of 2 hours and this temperature is maintained for 6 hours. After cooling to 25° C., the reaction mass is discharged onto ice in such a way that the temperature does not exceed 0° C. The suspension is filtered and the material on the filter is washed acid-free with ice-water.

(b) The moist filter cake, consisting of the aluminium complex of phthalocyanine-trisulphochloride, is stirred in 500 ml of ice-water and 32 g of 1-amino-3-dimethylaminopropane are added. After stirring for 15 hours at 20° to 30° C., the temperature is raised to 60° to 70° C. for a further 4 hours. The suspension is filtered and the residue is washed with 500 ml of warm water and dried in vacuo at 70° to 80° C. This gives the compound of the formula $$\text{Al Cl (PC)}\text{—}[SO_2NHCH_2CH_2CH_2N(CH_3)_2]_3 \qquad (601)$$

$\lambda max = 675.5$ nm (in $H_2O$, pH 7).

The compounds of the formula $$\text{Al Cl (PC)}\text{—}[SO_2\text{—}R]_3 \qquad (602)$$

listed in Table 3 which follows, can be obtained in an analogous manner by reacting the aluminium complex of phthalocyanine-trisulphochloride, obtained according to Example 6(a), with a corresponding amine.

TABLE 3

| Formula No. | R | Starting compound HR used |
|---|---|---|
| 603 | —NH—CH₂CH₂—N(CH₃)₂ | H₂N—CH₂CH₂N(CH₃)₂ |
| 604 | —NH—⌬—N(CH₃)₂ | H₂N—⌬—N(CH₃)₂ |

EXAMPLE 7

10 g of the zinc complex of phthalocyanine are heated in 120 g of chlorosulphonic acid at 130° to 132° C. for 3 hours. After cooling to 80° C., 20 ml of thionyl chloride are added dropwise to the solution in the course of one hour. After further stirring at 80° C., the solution is cooled to room temperature and poured onto 800 g of ice and 200 ml of water. The residue is filtered off and washed with ice-water and then suspended in 100 g of ice and 100 ml of water in the presence of 15 ml N-dimethylaminopropylamine. The suspension is further stirred for 1 hour at 80° C. After cooling to room temperature, the residue is filtered off, washed with water and dried in vacuo at 80° C. This gives 6.05 g of a product of the formula $$\text{ZnPC}\left[SO_2NHCH_2CH_2CH_2\text{—}N\begin{matrix}CH_3\\CH_3\end{matrix}\right]_3 \qquad (605)$$

Using the copper complex of phthalocyanine and, respectively, the nickel complex of phthalocyanine as the starting materials, the Cu and Ni complexes corresponding to formula (605) are obtained by the process just described.

EXAMPLE 8

20 g of the aluminium complex of phthalocyanine obtained according to Example 3(a) are stirred in 240 ml of 33% strength oleum for 7 hours at 73° to 75° C. The reaction mixture, which has been cooled to 25° C., is discharged onto a mixture of 1,000 g of ice and 200 g of sodium chloride. The temperature is kept at 0° to 20° C. by further addition of ice. The suspension is filtered and the filter residue is washed with a 10% strength sodium chloride solution until neutral. It is then also washed with 300 ml of 10% strength hydrochloric acid. The product is dried in vacuo at 80° C. The product obtained in this way has the formula

$\lambda$max = 671 nm (in $H_2O$, pH 9).

If the sulphonation described above is carried out using 40% strength oleum, this gives a product of the formula

$\lambda$max = 671.75 (in $H_2O$, pH 9).

EXAMPLE 9

Examples 4, 5 and 8 are repeated except that the zinc complex of phthalocyanine is used in place of the aluminium complex of phthalocyanine, as the starting material, affording the corresponding zinc complexes in place of the aluminium complexes of the formulae (401), (403) to (416), (501), (801) and (802).

EXAMPLE 10

Test to determine the activity against bacteria

Method:

A germ suspension of a specific species of bacteria is added to an aqueous solution which contains the phthalocyanine compound to be tested, in a specific concentration, the number of germs added being about $10^6$ germs/ml. This test suspension is in a glass beaker under a water-cooled sheet of glass, in order to prevent warming as a result of the subsequent exposure to light. The suspension is now irradiated for one hour with a filament lamp or an infra-red lamp*, which is at a distance of 20 cm above the surface of the suspension. In each case twice 0.1 ml of the suspension are then inoculated onto the surface of nutrient agar plates and the number of residual germs is determined. Conclusions regarding the effectiveness of the phthalocyanine compounds to be tested are drawn from the reduction in the germ count.

*Light sources which can be used are, for example, the following lamps:
(A) "Gloria" 200 watt, 2,800 lm filament lamp
(B) Philips IR, 250 watt, type 13372 E/479 infra-red lamp ("red") and
(C) Philips IR, 250 watt, type 13372 E/06 infra-red lamp ("white")

Results:

Experiment 1

The following phthalocyanines are tested: (PC=phthalocyanine)
(a) metal-free $PC(SO_3H)_2$
(b) $ZnPC(SO_3H)_2$
(c) $ZnPC(SO_3Na)_4$
(d) $AlClPC(SO_3H)_2$
(e) $CaPC(SO_3NH_4)_2$ and $CaPC(SO_3H)_{3-4}$
(f) $MgPC(SO_3NH_4)_2$ and $MgPC(SO_3H)_{3-4}$

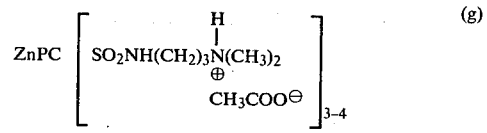

(h) $FePC(SO_3H)_2$ and $FePC(SO_3H)_{3-4}$.

Compounds a to h are employed in a concentration range between 0.005 and 100 ppm. Test germs used: Staph. aureus SG 511, Staph. aureus ATCC 6538 and Strept. faecalis var. zymogenes NCTC 5957.

The number of test germs is reduced by compounds a to h by up to 4 powers of ten at very low concentrations and by 6 powers of ten at higher concentrations.

EXPERIMENT 2

The Gram-negative strains: Escherichia coli NCTC 8196, Pseudomonas aeruginosa ATCC 15442 and Proteus vulgaris ATCC 6896 are used as test germs and the procedure is in accordance with the method described initially.

The acid compound d, which is tested, shows very good photo-deactivating properties against the above-mentioned Gram-negative germs when sodium chloride is added in a concentration of between 1 and 3%. A reduction in the germs of up to 5 powers of ten can be achieved in this way with concentrations of compound d of between 1 and 100 ppm.

EXPERIMENT 3

In the experiments described above, exposure to light is for one hour in each case.

In the present experiment, the exposure time is varied between 10 minutes and one hour, in 10 minute intervals. Active substance: compound d Test germ: Strept. faecalis var. zymogenes NCTC 5957.

It is found that the degree of reduction in the germs continuously increases for exposure times of between 10 and 40 minutes. The maximum value is reached at 40 minutes and remains constant on further exposure to light.

EXAMPLE 11

The procedure is in accordance with the method described in Example 10 and, in accordance with Experiment 1, the water-soluble phthalocyanine compounds of the formulae (401), (501), (601), (701), (801) and (802), and also the zinc complexes analogous to the compounds (401), (501), (801) and (802), are examined to determine their bactericidal action. Depending on the concentration employed, the said compounds effect an extensive reduction in the test germs employed.

Similarly good results are obtained with the compounds of the formulae (403) to (416) and (603) to (605)

and also the corresponding zinc, copper and nickel complexes and with the remaining phthalocyaninesulphonic acid complexes mentioned in Example 2 (for example the Cu and Ni complexes). The compounds of the formula $$\text{Al Cl (PC—[CH}_2\text{—R}_x]_v \qquad (1101)$$

listed in Table 4 which follows also show a good bactericidal action in the test carried out according to Example 10.

TABLE 4

| Formula No. | $R_x$ | v |
|---|---|---|
| 1102 | $-\overset{\oplus}{N}(CH_3)_3\ Cl^\ominus$ | 3 |
| 1103 | $-\underset{\underset{CH_3}{\mid}}{\overset{\overset{CH_3}{\mid}}{N}}-NH_2\ Cl^\ominus$ | 3 |
| 1104 | $-\overset{\oplus}{N}\!\!\diagup\!\!\diagdown\ Cl^\ominus$ | 3 |
| 1105 | $-S-C\overset{\diagup NH_2^\oplus}{\diagdown NH_2}\ Cl^\ominus$ | 2 |
| 1106 | $-\overset{\oplus}{S}=C\overset{\diagup N(CH_3)_2}{\diagdown N(CH_3)_2}\ Cl^\ominus$ | 3 |
| 1107 | $-\overset{\oplus}{N}\!\!\diagup\!\!\diagdown\!\!N\ Cl^\ominus$ | 3 |

EXAMPLE 12

Test to determine the disinfectant action on textiles:

A piece of cotton fabric is stretched on a glass rack and inoculated with a test suspension described in Example 10 (containing the active substance and a test germ strain). The glass rack, which is connected to a motor, is now rotated and irradiated with an infra-red lamp. A sheet of glass, which is cooled with running water, is placed between the lamp and the piece of fabric in order to prevent warming of the piece of fabric. In parallel to this, a piece of fabric to which, however, no microbicidal active substance had been applied, is treated under the same experimental conditions. After exposing to light for 1 hour, the germ counts are determined quantitatively and the reduction in germs effected by the particular phthalocyanine is found. The action of phthalocyanine compound d from Example 10, Experiment 1, towards Strept. faecalis var. zymogenes NCTC 5957 was tested. The same reduction in germs, as a function of the concentration employed, as in Example 10, Experiment 1 was found.

EXAMPLE 13

A piece of cotton fabric is treated at 80° C. in a liquor (liquor ratio 1:20) which contains 0.1 to 10 ppm of the compound of the formula (301), with 4 additions of NaCl (2.5%) at intervals of 10 minutes in each case. The fabric is then rinsed for 2 minutes in running cold water and dried for 1 hour at 80° C.

The cotton fabric finished in this way is now inoculated with, in each case, one germ suspension (*Staph. aureus* ATCC 6538 and *Strept. faecalis* ATCC 5957), stretched on a metal rack and exposed to light using the conditions and devices given below.

The irradiation lamp used is lamp "C" described in Example 10. Distance of the lamp from the fabric: 20 cm. Exposure time: 1 hour. The metal rack with the fabric stretched thereon is rotated by a motor (32 revolutions per minute) which is connected to it. Said metal rack is located below the water-cooled sheet of glass. The waterbath, which is temperature-controlled at about 50° C., is intended to prevent the suspension of bacteria from drying out and is located the metal rack. The water-cooled sheet of glass prevents warming of the fabric as a result of the exposure to light and is located below the irradiation lamp, separating said lamp from the metal rack with the fabric stretched thereon.

After exposure to light, the germ count is determined in the conventional manner by parallel counts. In each case, one piece of fabric which has been inoculated but not provided with a finish is also exposed as a control. The results are summarised in Table 5. The numerical values x give the particular reduction in germs in powers of ten in accordance with the formula $-\log_{10}(N/N_o)$, in which $N_o$ is the number of germs added and N is the number of surviving germs (average values from 5–10 parallel counts).

TABLE 5

| | Concentration of compound (301) in the liquor | | | | | | | |
|---|---|---|---|---|---|---|---|---|
| | 0 | 0.1 | 1 | 2 | 3 | 4 | 5 | 10 |
| Staph. aureus ATCC 6538 | $\bar{x}$ | 0 | 0 | 2.3 | 3.2 | 3.3 | 3.3 | 3.7 | $\geq$4.5 |
| Strept. faecalis ATCC 5957 | $\bar{x}$ | 0 | 0.2 | 2.7 | 4.1 | $\geq$4.3 | $\geq$4.3 | $\geq$4.3 | $\geq$4.3 |

If the compound of the formula (301) is replaced by the other water-soluble phthalocyanine derivatives tested in Examples 10 and 11 in the suspension experiment and fabric is treated in the manner just described, fabric having a similarly good antibacterial finish is obtained.

What is claimed is:

1. A process for combatting microorganisms in or on organic or inorganic substrates and for protecting said substrates against attack by microorganisms, which comprises treating the substrates with an effective amount of a watersoluble phthalocyanine derivative, which is a metal-free phthalocyanine derivative or a metal complex thereof which contains, as the metal atom, aluminum, zinc, iron-II, calcium, magnesium, sodium or potassium, said derivative contains, as groups conferring solubility in water, sulpho or carboxyl groups and their salts, or groups of the formulae

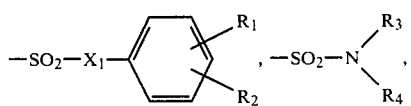

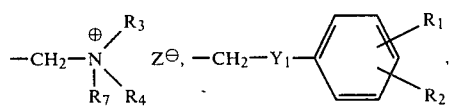

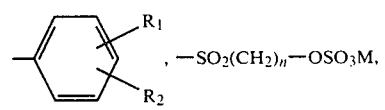

-continued

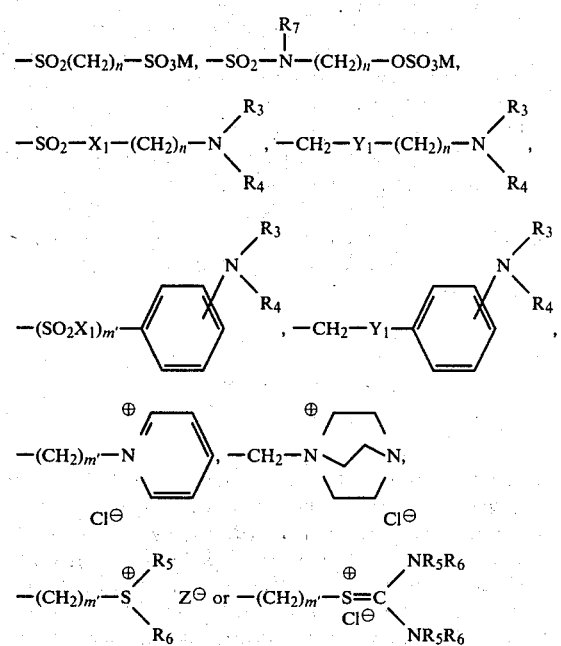

in which formula $X_1$ is oxygen or a —NH— or —N-alkyl radical and $R_1$ and $R_2$ independently of one another are hydrogen, a sulpho groups and salts thereof, a carboxyl group and salts thereof or a hydroxyl group, at least one of the radicals $R_1$ and $R_2$ being a sulpho or carboxyl group or a salt thereof, $Y_1$ is oxygen, sulphur or a —NH— or —N-alkyl radical, $R_3$ and $R_4$ independently of one another are hydrogen, alkyl, hydroxyalkyl, cyanoalkyl, sulphoalkyl, carboxyalkyl or halogenoalkyl having 1 to 6 carbon atoms, unsubstituted phenyl or phenyl substituted by halogen, alkyl or alkoxy having 1 to 4 carbon atoms, sulpho or carboxyl, or $R_3$ and $R_4$ together with the nitrogen atom to which they are bonded are a saturated 5-membered or 6-membered heterocyclic ring, which additionally can also contain a nitrogen atom or oxygen atom as a ring member, $R_5$ and $R_6$ independently of one another are substituted or unsubstituted alkyl or aralkyl radical, $R_7$ is a substituted or unsubstituted alkyl group having 1 to 6 carbon atoms, or hydrogen, M is an alkali metal ion or ammonium ion, $Z^\ominus$ is an anion, for example a chlorine, bromine, alkylsulphate or aralkyl-sulphate ion, n is an integer from 2 to 12 and m' is 0 or 1, the number of groups conferring solubility in water, which can be of the same type or different, being at least sufficiently large to ensure that an adequate solubility in water is obtained, said phthalocyanine derivative also optionally containing other substitutes in addition to the groups conferring solubility in water, the amount of said phthalocyanine derivative employed being insufficient to cause substantial discoloration of the substrate, in the presence of oxygen and water and with concurrent irradiation with light in the infra-red and/or visible range of sufficient intensity to effect disinfection.

2. A process according to claim 1, which comprises carrying out the process in the presence of an inorganic salt.

3. A process according to claim 1 for combating bacteria.

4. A process according to claim 1 for disinfecting swimming pools and effluents from sewage treatment plants, which comprises adding 0.001 to 100 ppm of one or more of the phthalocyanine derivatives.

5. A process according to claim 1 which comprises using, as the water-soluble phthalocyanine derivative, a derivative of the formula

in which PC is the phthalocyanine ring system, v has any desired value between 1 and 4, Me is Zn, Fe(II), Ca, Mg, Na, K or AlX, in which X is an anion, m is 0 or 1 and R is a group of the formula

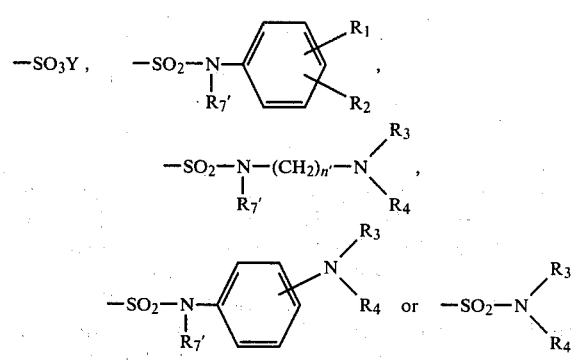

in which Y is hydrogen or an alkali metal, ammonium or amine ion, $R_7'$ is hydrogen or alkyl having 1 to 4 carbon atoms, n' is an integer from 2 to 6, $R_1$ and $R_2$ independently of one another are hydrogen, a sulpho group and salts thereof, a carboxyl group and salts thereof or a hydroxyl group and at least one of the radicals $R_1$ and $R_2$ is a sulpho or carboxyl group or a salt thereof, and $R_3$ and $R_4$ independently of one another are hydrogen, alkyl, hydroxyalkyl, cyanoalkyl, sulphoalkyl, carboxyalkyl or halogenoalkyl having, in each case, 1 to 6 carbon atoms, or phenyl, or $R_3$ and $R_4$ together with the nitrogen atom to which they are bonded are a saturated 5-membered or 6-membered heterocyclic ring, which additionally can also contain a nitrogen atom or oxygen atom as a ring member, and, when several radicals R are present in the molecule, these radicals can be identical or different, and all the radicals R are bonded to the phenyl nuclei of the phthalocyanine ring system.

6. A process according to claim 5, which comprises using, as the water-soluble phthalocyanine derivative, a derivative of the formula

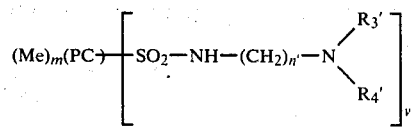

in which PC, Me and m are as defined in claim 5, n' is an integer between 2 and 6, $R_3'$ and $R_4'$ independently of one another are hydrogen, phenyl, sulphophenyl, carboxyphenyl or alkyl, hydroxyalkyl, cyanoalkyl, sulphoalkyl, carboxyalkyl or halogenoalkyl having, in each case, 1 to 6 carbon atoms, or together with the nitrogen atom are the morpholine ring, and v is a number between 1 and 4, and, if v>1, the radicals

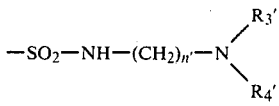

present in the molecule can be identical or different.

7. A process according to claim 5, which comprises using, as the water-soluble phthalocyanine derivative, a derivative of the formula

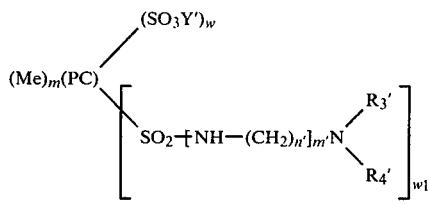

in which PC, Me and m are as defined in claim 5, Y' is hydrogen or an alkali metal or ammonium ion, n' is an integer between 2 and 6, $R_3'$ and $R_4'$ independently of one another are hydrogen, phenyl, sulphophenyl, carboxyphenyl or alkyl, hydroxyalkyl, cyanoalkyl, sulphoalkyl, carboxyalkyl or halogenoalkyl having, in each case, 1 to 6 carbon atoms, or together with the nitrogen atom are the morpholine ring, m' is 0 or 1 and w and $w_1$ independently of one another are any desired number between 0.5 and 3, and $w+w_1$ is at least 1, but at most 4.

8. A process according to claim 1, which comprises carrying out the treatment of the particular substrate in an aqueous bath which contains the water-soluble phthalocyanine active compound in a concentration of 0.1 to 50 mg/l.

9. A process according to claim 8, which comprises carrying out the irradiation with a filament lamp or infra-red lamp, either in the treatment bath or outside the treatment bath.

10. A process according to claim 8, which comprises irradiating the substrate in sunlight.

11. A process according to claim 1 for combating microorganisms on textile materials and for protecting the said materials against attack by micro-organisms, which comprises treating these materials, in the presence of oxygen and while irradiating with visible or infra-red light, with an aqueous solution which contains said phthalocyanine derivative.

12. A process according to claim 11 for disinfecting goods to be washed, which comprises washing the goods to be washed, while irradiating with infra-red or visible light, in a wash liquor which contains, in addition to conventional constituents of washing agents, 0.001 to 100 ppm of one or more of the phthalocyanine derivatives.

13. A process according to claim 11 for disinfecting or finishing textiles, which comprises treating the latter in a liquor which contains 0.01 to 50 ppm of said phthalocyanine derivative, the bath being irradiated direct with an artificial light source or the textiles, in the damp state, subsequently being irradiated with an artificial light source or exposed to sunlight.

14. A process according to claim 1, which comprises using a phthalocyanine derivative, or a metal complex thereof, which is substituted on the phenyl nuclei by said acid or basic groups.

15. A process according to claim 14, which comprises using, as a phthalocyanine derivative having basic substituents, or a metal complex thereof, a derivative or complex in which the phenyl nuclei contain sulphanoyl or alkoxysulphonyl groups having basic substituents and/or quaternary ammonium groups, the total number of substituents being between 2 and 4.

16. A process according to claim 15, which comprises using a phthalocyanine derivative, or a metal complex thereof, which carries, on the phenyl nuclei, substituents of the formula

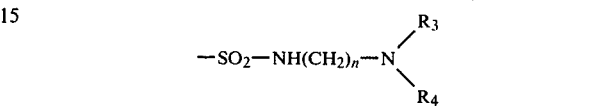

in which n is a number between 2 and 12 and $R_3$ and $R_4$ independently of one another are hydrogen, alkyl, hydroxyalkyl, cyanoalkyl or halogenoalkyl having, in each case, 1 to 12 carbon atoms, or $R_3$ and $R_4$ together with the nitrogen atom to which they are bonded form a saturated 5-membered or 6-membered heterocyclic ring, which if desired can additionally also contain a nitrogen atom or oxygen atom as a ring member.

17. A process according to claim 14, which comprises using a metal-free phthalocyanine derivative.

18. A process according to claim 17, which comprises using a phthalocyanine derivative of the formulae defined in claims 8, 11 or 12, in which m is 0.

19. A process according to claim 14, which comprises using a metal complex of a phthalocyanine derivative.

20. A process according to claim 19, which comprises using an aluminium or zinc complex of a phthalocyanine derivative.

21. A process according to claim 14, which comprises using, as a phthalocyanine derivative having acid substituents, or a metal complex thereof, a derivative or complex which is substituted by sulpho groups and/or carboxyl groups or radicals containing such groups.

22. A process according to claim 21, which comprises employing a sulphonated phthalocyanine or a metal complex thereof.

23. A process according to claim 22, which comprises using the aluminium or zinc complex of a sulphonated phthalocyanine having a degree of sulphonation of 1 to 4 and preferably 1.5 to 4.

24. A process according to claim 22, which comprises using a sulphonated phthalocyanine derivative of the formula

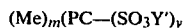

$(Me)_m(PC-(SO_3Y')_v$ in which PC is the phthalocyanine ring system, Y' is hydrogen or an alkali metal or ammonium ion, v is any desired number between 1 and 4 (the degree of sulphonation), m is 0 or 1 and Me is Zn, Fe(II), Ca, Mg, Na, K or AlX, in which X is an anion, especially a halide, sulphate, hydroxyl or acetate ion.

25. A process according to claim 24, which comprises using a phthalocyanine derivative in which m is 1 and Me is Zn or AlX.

26. A process according to claim 25, which comprises using a phthalocyanine derivative in which m is 1 and Me is AlX.

* * * * *